(12) United States Patent
Cheuk et al.

(10) Patent No.: US 8,563,029 B2
(45) Date of Patent: Oct. 22, 2013

(54) EXOPOLYSACCHARIDE CONTAINING FOOD

(75) Inventors: Wai Cheuk, San Marcos, CA (US); Christina Khoo, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 521 days.

(21) Appl. No.: 12/049,546

(22) Filed: Mar. 17, 2008

(65) Prior Publication Data

US 2008/0160164 A1 Jul. 3, 2008

Related U.S. Application Data

(62) Division of application No. 10/942,397, filed on Sep. 16, 2004.

(51) Int. Cl.
*A61K 47/00* (2006.01)

(52) U.S. Cl.
USPC ............................................. 424/439

(58) Field of Classification Search
None
See application file for complete search history.

(56) References Cited

U.S. PATENT DOCUMENTS

| | | | | |
|---|---|---|---|---|
| 4,037,000 A * | 7/1977 | Burge et al. | ...... | 426/572 |
| 4,410,551 A | 10/1983 | Comer | | |
| 4,647,470 A * | 3/1987 | Sanderson et al. | ...... | 426/573 |
| 4,822,626 A | 4/1989 | Spanier et al. | | |
| 4,942,042 A | 7/1990 | Bhargava | | |
| 5,079,024 A * | 1/1992 | Crane | ...... | 426/573 |
| 5,158,800 A * | 10/1992 | Bell | ...... | 426/660 |
| 5,292,534 A | 3/1994 | Vlentine et al. | | |
| 5,339,771 A | 8/1994 | Axelrod | | |
| 5,372,829 A * | 12/1994 | Chalupa et al. | ...... | 426/293 |
| 5,380,522 A | 1/1995 | Day | | |
| 5,419,283 A | 5/1995 | Leo | | |
| 5,456,937 A | 10/1995 | Chalupa | | |
| 5,571,545 A * | 11/1996 | Yokoyama et al. | ...... | 426/93 |
| 5,596,084 A | 1/1997 | Sanderson et al. | | |
| 5,616,569 A | 4/1997 | Reinhart | | |
| 5,795,585 A | 8/1998 | Ikeda et al. | | |
| 5,869,118 A | 2/1999 | Morris et al. | | |
| 5,895,804 A | 4/1999 | Lee et al. | | |
| 5,951,984 A | 9/1999 | Kaneko et al. | | |
| 6,280,779 B1 | 8/2001 | Nadeau et al. | | |
| 6,410,079 B2 * | 6/2002 | Cheuk et al. | ...... | 426/641 |
| 6,426,195 B1 | 7/2002 | Zhong et al. | | |
| 6,458,404 B1 | 10/2002 | Adachi | | |
| 2002/0039615 A1 | 4/2002 | Adachi | | |
| 2003/0167675 A1 | 9/2003 | Noguchi et al. | | |
| 2004/0131745 A1 | 7/2004 | Fernandes et al. | | |
| 2005/0004071 A1 | 1/2005 | Comper | | |

FOREIGN PATENT DOCUMENTS

| | | |
|---|---|---|
| CA | 2547330 | 6/2005 |
| CN | 1395938 | 2/2003 |
| EP | 0290251 B1 | 11/1988 |
| EP | 0291228 A1 | 11/1988 |
| EP | 0323008 B1 | 7/1989 |
| EP | 0382355 A | 8/1990 |
| EP | 0454373 A2 | 10/1991 |
| EP | 0462426 B1 | 12/1991 |
| EP | 0630580 A2 | 12/1994 |
| EP | 0685170 A2 | 12/1995 |
| EP | 0907664 B1 | 4/1999 |
| EP | 1029456 A1 | 8/2000 |
| EP | 1048690 A1 | 11/2000 |
| JP | 2144067 | 6/1990 |
| JP | 2-289520 | 11/1990 |
| JP | 8157377 | 6/1996 |
| JP | 9187493 | 7/1997 |
| JP | 9201170 | 8/1997 |
| JP | 9275973 | 10/1997 |
| JP | 10067625 | 3/1998 |
| JP | 10179050 | 7/1998 |
| JP | 11253114 | 9/1999 |
| JP | 2001269125 | 10/2001 |
| JP | 2003259817 | 9/2003 |
| WO | WO99/64468 | 12/1999 |
| WO | WO00/31146 | 6/2000 |
| WO | WO01/33975 A | 5/2001 |
| WO | WO 02/070670 | 9/2002 |
| WO | WO 02087356 A1 | 11/2002 |
| WO | WO03/045401 A | 6/2003 |
| WO | WO03/068004 | 8/2003 |
| WO | WO 2004/077281 | 9/2004 |
| WO | WO2004/080206 A | 9/2004 |
| WO | WO2005/004989 | 1/2005 |
| WO | WO2005/053425 A | 6/2005 |

OTHER PUBLICATIONS

Dog Nutritional Needs; accessed at www.gopetsamerica/dog-health/dog_nutritional_needs.aspx.*
Mochizuki et al., 1999, "Feline Coronavirus Participation in Diarrhea of Cats," J. Veterinary Medical Science 16(9):1071-1073.
Anonymous, 2002, Gist of Convention of Japan Society for Bioscience, Biotechnology, and Agrochemistry, p. 238, Abstract 4-2Ga06.
Shuji et al., 2003, "Contemporary Condition and Foresight of Thickening and Stabilizing Agent Market," Monthly Food Chemical 19(8):37-41.
Database WPI Week 199641 Dewert Publications LTD.London, GB: An 1996-408319 (XP002483361).
Database WPI Week 199418 Dewert Publications LTD.London, GB: An 1994-146955 (XP002483362).
Anderson et al. The dietaty effects if Gellan Gum in humans, Food additives and Contaminants, 1988, vol. 5, No. 3, 237-245.

(Continued)

Primary Examiner — Anand Desai
Assistant Examiner — Melissa Mercier
(74) Attorney, Agent, or Firm — Thomas M. Hunter

(57) ABSTRACT

Compositions (including pharmaceutical compositions, foods, supplements, toys and treats) comprising a microbial exopolysaccharide are provided as well as methods for preventing or reducing diarrhea in a mammal wherein the method comprises administering a therapeutically amount of a microbial exopolysaccharide to a mammal in need thereof.

7 Claims, No Drawings

(56) References Cited

OTHER PUBLICATIONS

Lin FSD, Gellan Gum: Kelco Inc. Toxicological Review and Evaluation, entire document, Jan. 16, 2002.

Anderson DMW, The dietary effects of gellan gum in humans, Nov. 20, 1987, entire document.

Giavasis I et al. "Gellan Gum," Crit Rev. Biotechnol., 20(3):177-211;2000.

Shimizu J, et al. "Curdlan and Gellan Gum, Bacterial Gel-Forming Polysaccharides, Exhibit Different Effects on Lipid Metabolism, Cecal Fermentation and Fecal Bile Acid Excretion in Rats," J. Nutr. Sci. Vitaminol, 45(3):251-62;1999.

Sun W, et al., "Survival of Bifidobacteria in Yogurt and Simulated Gastric Juice Following Immobilization in Gellan-Xanthan Beads," Int. J. Food Microbial, 61(1):17-25;2000.

Sutherland I, "Novel and Established Applications of Microbial Polysaccharides,"TIBTECH, 16:41-46; 1998.

Tetsuhuchi M, et al., Effects of Curdian and Gellan Gum on the Surface Structure of Instenial Muccosa in Rats,: J. Nutr. Sci. Vitaminol, 43(5):515-27; 1997.

International Search Report for PCT/US2004/006358, Mar. 2, 2004.

"Prevention and treatment of an acute traveler's diarrhea" //published on May 27, 2004 at "antibiotic.ru" website// from the source: Connor B.A. et al. "Prevention and treatment of acute traveler's diarrhea" Infect Med 2004; 21(1): 18-9 [online] (found on Dec. 14, 2009 in the Internet: http://www.antibiotic.ru/index.php?article=904.

Gracheva, L., "Antibacterial Therapy in Mucoviscidosis," Russian Medical Journal, Feb. 3, 1998, vol. 6, No. 3, [online] [Found on Dec. 11, 2009] found in the Internet: http://www.rmj.ru/articles_2038.htm.

Volova T.G. "Biotechnology" SO RAN publishers, Novosibirsk, 1999, "Biopolymers", pp. 81-82 [online] [Found on Dec. 9, 2009] in the Internet: http://window.edu.ru/window_catalog/files/r26462/krasu009.pdf.

Zaprudnov A. et al. "Diarrhea in children" //Medical gazette, No. 54 of Jul. 16, 2004 [online] (found Jul. 31, 2009 in the Internet): http://medgazeta.rusmedserv.com/2004/54/article_1053.html.

"Prevention and treatment of an acute traveler's diarrhea" //published on May 27, 2004 at "antibiotic.ru" website// from the source: Connor B.A. et al. "Prevention and treatment of acute traveler's diarrhea" Infect Med 2004; 21(1): 18-9 [online] (found on Dec. 14, 2009 in the Internet.

Association of American Feed Control Officials Official Publication, p. 220, 2003.

Gracheva, L., "Antibacterial Therapy in Mucoviscidosis," Russian Medical Journal, Feb. 3, 1998, vol. 6, No. 3, [online].

Shaoul R. et al. "An update on probiotics and prebiotics in children". Harefuah. May 2004; 143(5): 377-81, 389, abstract (found Jul. 30, 2009 at Pubmed. PMID: 15190853.

Volova T.G. "Biotechnology" SO RAN publishers, Novosibirsk, 1999, "Biopolymers", pp. 81-82.

Zaprudnov A. et al. "Diarrhea in children" //Medical gazette, No. 54 of Jul. 16, 2004 [online].

* cited by examiner

EXOPOLYSACCHARIDE CONTAINING FOOD

CROSS-REFERENCE TO RELATED APPLICATIONS

This application is a Divisional application of U.S. patent application Ser. No. 10/942,397, filed Sep. 16, 2004.

FIELD OF THE INVENTION

This invention is directed generally to methods for preventing or reducing diarrhea in a mammal. This invention also is directed generally to compositions (including pharmaceutical compositions, foods, supplements, treats, toys, etc.) for administration to or consumption by a mammal for the prevention or reduction of diarrhea.

BACKGROUND OF THE INVENTION

All mammals require a healthy diet and proper digestion for continued growth and ordinary well being. However, gastrointestinal distress interferes with the ordinary digestion of food. Some of these problems can be quite serious and demand serious medical attention such as Crohn's disease; irritable bowel syndrome, other chronic conditions and the like. Others are of a less serious condition and can be essentially self-limiting such as food borne virus, intestinal flu and the like. Almost all gastrointestinal disorders are accompanied by diarrhea, a loose watery stool which can be extremely unpleasant to the mammal harboring the condition or to a pet owner who must clean up after the pet evacuates, particularly if on a chronic basis.

It has also been found that some pet foods tend to create or exacerbate a diarrhea condition. For example, as described in U.S. Pat. No. 6,280,779 issued Aug. 28, 2001, diarrhea can be a significant problem with pets consuming a "chunks and gravy" diet. In particular, the presence of significant quantities of gum in a "chunks and gravy" diet, primarily chemically modified starches or gums, but even, to a lesser extent, ordinary natural starches and gums has been associated with diarrhea in pets.

SUMMARY OF INVENTION

This invention is directed to compositions and methods for preventing or reducing diarrhea in a mammal.

Briefly, therefore, this invention is directed, in part, to a method for preventing or reducing diarrhea in a mammal. The method comprises administering a therapeutically effective amount of a microbial exopolysaccharide to a mammal in need thereof.

In one contemplated embodiment, the microbial exopolysaccharide is selected from the group consisting of rhamsan, curdlan, xanthan gum, scleroglucan, PS-10 gum, PS-21 gum, PS-53 gum, polysaccharides from *Alcaligenes* sp., PS-7 gum, gellan gum, curdlan, bacterial alginate, dextran, pullulan, baker's yeast glycan, bacterial cellulose, 6-deoxy-hexose-containing polysaccharides and combinations thereof.

In another contemplated embodiment, the microbial exopolysaccharide is administered orally in the diet of a human.

In another contemplated embodiment, the microbial exopolysaccharide is administered orally in the diet of a companion animal.

This invention also is directed to a pharmaceutical composition useful in preventing or reducing diarrhea in a mammal. The composition comprises a therapeutically effective amount of a microbial exopolysaccharide and a pharmaceutical carrier.

This invention also is directed to a composition for animal consumption wherein the composition comprises at least one food component; and at least about 0.1% of a microbial exopolysaccharide (based on the dry weight of the composition).

This invention also is directed to a method for preventing or reducing diarrhea in an animal. The method comprises feeding the animal a composition comprising at least one food component; and at least about 0.1% of a microbial exopolysaccharide (based on the dry weight of the composition).

This invention also is directed to an animal treat, wherein the treat comprises a microbial exopolysaccharide.

This invention also is directed to an animal toy, wherein the toy comprises a microbial exopolysaccharide.

This invention also is directed to a wet food composition suitable for ingestion by a dog or cat and having at least one food component and a diarrhea preventing or diarrhea reducing amount of a microbial exopolysaccharide, preferably a microbial exopolysaccharide comprising a gellan gum.

Further benefits of Applicants' invention will be apparent to one skilled in the art from reading this patent.

DETAILED DESCRIPTION OF THE PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

It has been found as set forth in this invention that the inclusion of a microbial exopolysaccharide in a mammal's diet can be useful to reduce or prevent diarrhea. Specifically, the administration of microbial exopolysaccharides has been shown to prevent diarrhea in a mammal that has a tendency to have diarrhea from time to time and to reduce diarrhea in a mammal already experiencing diarrhea. In particular, for mammals experiencing diarrhea, the reduction in diarrhea can vary widely. For example, Applicants have discovered that the administration of the compositions and methods of the present invention to a mammal experiencing diarrhea can result in a simple visual observation of reduction to a statistically significant reduction to a virtual elimination or rollback of the diarrhea state. Further, such beneficial effects have been observed in almost all etiologies which are at least partially characterized by a state of diarrhea including etiologies that are unknown or induced through a bacterial, viral (both preferably short term) or a dietary regimen.

It is contemplated that the compositions and methods of this invention may be useful for a variety of mammals, including humans, non-human mammals such as non-human primates (e.g., monkeys, chimpanzees, etc.), companion animals (e.g., dogs, cats, equine, etc.), farm animals (e.g., goats, sheep, swine, bovine, etc.), laboratory animals (e.g. mice, rats, etc.) and wild and zoo animals (e.g., wolves, bears, deer, etc.).

In some embodiments of this invention, for example, the mammal is a human. In other embodiments of this invention, the mammal is a companion animal. In other embodiments of this invention, the mammal is a dog. In other embodiments, the mammal is a cat.

This invention contemplates a wide variety of microbial exopolysaccharide-containing compositions. Contemplated compositions include, for example, pharmaceutical compositions, foods, supplements, treats and toys (particularly chewable and consumable toys).

In some embodiments, the microbial exopolysaccharide-containing composition is a food. Although both liquid and solid foods are contemplated, solid foods are typically preferred. Where the food is solid, the microbial exopolysaccharide may be coated on the food, incorporated into the food, or both. Contemplated foods include both dry foods or wet foods.

In one contemplated embodiment, the composition is a food for animal consumption and comprises both a food component and a microbial exopolysaccharide. In a preferred embodiment, the food component is selected from the group consisting of meat, a meat by-product, a daily product and an egg product. In another preferred embodiment, the food component is sufficient to meet the nutritional needs of a cat or a dog.

In another embodiment, the microbial exopolysaccharide-containing composition is a gel.

In another embodiment, the composition comprises an animal feed supplement. Supplements include, for example, a feed used with another feed to improve the nutritive balance or performance of the total. Contemplated supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials. Incorp. Official Publication, p. 220 (2003). Supplements may be in various forms including, for example, powders, liquids, syrups, pills, encapsulated compositions, etc.

In another embodiment, the composition comprises an animal treat. Treats include, for example, compositions that are given to an animal to entice the animal to eat during a non-meal time. Contemplated treats for canines include, for example, dog bones. Treats may be nutritional, wherein the composition comprises one or more nutrients, and may, for example, have a composition as described above for food. Non-nutritional treats encompass any other treats that are non-toxic. The microbial exopolysaccharide can be coated onto the treat, incorporated into the treat, or both.

In another embodiment, the composition comprises a toy. Toys include, for example, chewable toys. Contemplated toys for dogs include, for example, artificial bones. The microbial exopolysaccharide can form a coating on the surface of the toy or on the surface of a component of the toy, be incorporated partially or fully throughout the toy, or both. In a contemplated embodiment, the microbial exopolysaccharide is orally accessible by the intended user. There a wide range of suitable toys currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). It should be recognized that this invention contemplates both partially consumable toys (e.g., toys comprising plastic components) and fully consumable toys (e.g., rawhides and various artificial bones). It should be further recognized that this invention contemplates toys for both human and non-human use, particularly for companion, farm, and zoo animal use, and particularly for dog or cat use.

Examples of suitable microbial exopolysaccharides for use in the present invention generally include those microbial exopolysaccharides synthesized from bacteria selected from the group consisting of *Sphingomonas paucimobilis, Agrobacterium biovar, Xanthomonas campestris, Alcaligenes* sp., *Aureobasidium pullulans, Acetobacter xylinum, Sclerotium rolfsii, Schizophyllum commune, Saccharomyces cerevisiae* and *Sclerotium glucanicum*. More particularly, suitable microbial exopolysaccharides may include, for example, rhamsan, curdlan, xanthan gum, scleroglucan, PS-10 gum, PS-21 gum, PS-53 gum, polysaccharides from *Alcaligenes* sp., PS-7 gum, gellan gum, curdlan, bacterial alginate, dextran, pullulan, baker's yeast glycan, bacterial cellulose, 6-deoxy-hexose-containing polysaccharides and mixtures of the above.

In a preferred embodiment, the microbial exopolysaccharide comprises a gellan gum. Gellan gum is a linear polysaccharide made from fermentation by *Sphingomonas paucimobilis* (elodea) (ATCC31461). Industrial preparation of the gum can be carried out by inoculating *Sphingomonas paucimobilis* into a fermentation broth containing glucose, glucuronic acid and rhamnose to form a tetrasaccharide repeating unit in a ratio of 2:1:1. In its native form, gellan gum is highly acylated with 1.5 acyl group, acetyl and glycerate, per repeating unit. Modifications of the acyl groups both in number and type can be made as long as the basic anti diarrhea activity of the gellan gum is not significantly diminished. These different forms can be obtained from CP Kelco under different tradenames including Gelrite®, K9A50 and other Kelco gellan gums including but not limited to, Kelcogel LT®, Kelcogel F, and Kelcogel LT100®. As used throughout the specifications "gellan" refers to the natural gum or acyl modified gum as long as the anti-diarrhea function is maintained.

In the methods of the present invention, the microbial exopolysaccharide can be administered to the mammal, preferably one in need of such administration in any one of many ways, such as oral, rectal, and the like. Preferably, the microbial exopolysaccharide is administered orally. The microbial exopolysaccharide can be administered in a wet diet, either incorporated therein or on the surface of any diet component, such as, by spraying or precipitation thereon. It can be present in the nutritional diet per se or in a snack or a treat. It can also be present in the liquid portion of the diet such as water or another fluid. The microbial exopolysaccharide can be administered as a powder solid or as a liquid such as a gel. If desired the microbial exopolysaccharide can be orally administered in a pharmaceutical dosage form such as a capsule, tablet, caplet, syringe, and the like. Within the dosage form the microbial exopolysaccharide can be present as a powder or a liquid such as a gel. Any of the usual pharmaceutical carriers can be employed such as water, glucose, sucrose and the like together with the microbial exopolysaccharide.

With respect to administering the microbial exopolysaccharide to a dog or cat, the daily dosage minimum is at least about 0.1% by weight of food or at least about 0.05 g/kg body weight, preferably at least about 0.2% by weight, most preferably at least about 0.5% by weight or at least about 0.3 g/kg body weight. The maximum amount is below that which can bring about significant undesirable side effects. Generally no more than about 1.5 or 2% by weight of food and no more than about 4% by weight of the food or 1 or 2 g/kg body weight can be employed. A minimum dosage for administering the microbial exopolysaccharide to a human is about 0.05 g/kg body weight or preferably at least about 0.1 g/kg body weight. The maximum amount is below that which can bring about significant undesirable side effects. Generally no more than about 1 or 2 g/kg body weight of about 4% by weight of the food can be employed.

It is important to note that even when the cause of the diarrhea seems to be a food component, the component need not be removed completely or to any great extent from the diet for the microbial exopolysaccharide to be effective in combating the diarrhea.

EXAMPLES

The following examples are merely illustrative, and not limiting to this disclosure in any way.

Example 1

Twelve adult domestic shorthair cats (eight males and four females) with chronic diarrhea were placed on a canned control and test diet. The diets were similar in composition except for the substitution of the 0.2% Kelgum with 1% gellan gum blend (37% gellan gum, 33% sucrose, 18% calcium lactate) or 0.4% pure gellan gum. During the study the cats which were normally on prednisone were weaned off the prednisone 5 days prior to starting the study. The composition of the diets are shown in Table 1:

TABLE 1

| Nutrient | Control % of diet | Test % of diet |
| --- | --- | --- |
| Protein | 8.24 | 7.94 |
| Fat | 9.58 | 9.85 |
| Crude Fiber | 0.3 | 0.2 |
| Moisture | 72.7 | 72.6 |
| Ash | 2.05 | 2.11 |
| Calcium | 0.5 | 0.5 |
| Magnesium | 0.024 | 0.024 |
| Phosphorus | 0.28 | 0.26 |
| Phosphorus | 0.28 | 0.26 |
| Potassium | 0.22 | 0.24 |
| Sodium | 0.073 | 0.094 |
| Chloride | 0.22 | 0.23 |

In a double crossover design, 6 cats were fed the control diet and 6 cats were fed a test diet for 14 days followed by a washout period of another 14 days when all cats in the study were fed a washout diet. The cats were then crossed over to either the control or test diet for another 14 days. Stools were observed and graded every day during the study.

Stools were observed for the physical condition and graded based on the physical nature of the fecal matter. Grades were assigned a number ranging from 1 to 5 as follows:

Grade 1: Greater than two-thirds of the feces in the defecation are liquid. The feces have lost all form, appearing as a puddle or squirt.

Grade 2: Solid-liquid feces are an intermediate between soft and liquid feces. Approximately equal amounts of feces in defecation are soft and liquid.

Grade 3: Greater than two-thirds of the feces in a defecation are soft. The feces retain enough form to pile but have lost their firm cylindrical appearance.

Grade 4: Finn-soft feces are an intermediate between the grades of firm and soft. Approximately equal amounts of feces in a defecation are firm and soft.

Grade 5: Greater than two-thirds of the feces in a defecation are firm. The feces have a cylindrical shape with little flattening.

Generally, grades 1 and 2 are unacceptable while grades 4 and 5 are preferred.

Results of the study showed that there was a significant decrease in the frequency of stool scores 1 and 2 with consumption of the test diet compared to control diet. In particular, 23% of the feces from cats consuming the control diet had a stool score of 1 or 2 whereas only 4% of the feces from cats consuming the test diet scored a 1 or 2. Further, there was a large increase in the frequency of stool scores rated 4 and 5 from cats consuming the test diet as compared to cats consuming the control diet. 49%, of the feces from cats consuming the test diet rated a 4 or 5 whereas only 27% of the feces from cats consuming the control diet rated a 4 or 5. Prior to beginning the test diet, the average stool score was 2.7. With the test diet, the average stool score increased to 3.9.

Example 2

12 cats with chronic diarrhea were used in the study. 6 cats were each fed test diets or control diets similar to those described in Example 1 for 14 days. The test diets differed from those described in Example 1 as they included 0, 0.2, 0.3 and 0.40) gellan gum in the formula respectively. Stools were observed daily and graded as described in Example 1 throughout the experiment. Table 2 shows the percent occurrence of the different types of stool within each diet.

TABLE 2

| Dose of gellan | Stool Rating | | | | |
| --- | --- | --- | --- | --- | --- |
| (% formula) | 1 | 2 | 3 | 4 | 5 |
| 0.4 | 1% | 2% | 25% | 39% | 33% |
| 0.3 | 0% | 18% | 34.5% | 26% | 18% |
| 0.2 | 1% | 17% | 51% | 18% | 12% |
| 0.1 | 0% | 13% | 48% | 19% | 20% |
| Control | 13% | 16% | 47% | 18% | 1% |

The results showed that gellan gum at a concentration of 0.4% of the diet was able to prevent the incidence of diarrhea (stools 1-2) while at a concentration of 0.1 to 0.3% of the diet, gellan gum was able to reduce the incidence of diarrhea by 2 fold compared to control.

Example 3

Dogs fed a grocery brand chunks and gravy formula have been shown to have a significant incidence of diarrhea. This model was used to test the efficacy of gellan gum in reducing the occurrence of diarrhea in dogs. Dogs were fed the grocery brand chunks and gravy formula for 7 days in the control group. In the test group, the dogs were fed the same chunks and gravy formula with 0.4% gellan gum added to the food in the form of a gel. Stool were observed for 7 days and graded as described in Example 1. Table 3 shows the results of the test wherein adding gellan gum to the diet prevented the occurrence of diarrhea in this model.

TABLE 3

| | Stool Rating | | | | |
| --- | --- | --- | --- | --- | --- |
| | 1 | 2 | 3 | 4 | 5 |
| Control | 24% | 30% | 24% | 18% | 5% |
| Control with 0.4% gellan gum | 0% | 0% | 18% | 48% | 35% |

Example 4

The experiment described in Example 3 was conducted using a different chunks and gravy formula for the model of canine diarrhea. Further, gellan gum was incorporated in the gravy formula at different levels. The gravy was formulated with 1% guar gum for the control and test diets. Stools were observed daily and graded as described in Example 1. The results are shown below:

TABLE 4

|  | Stool Rating | | | | |
| --- | --- | --- | --- | --- | --- |
|  | 1 | 2 | 3 | 4 | 5 |
| Control | 18% | 9% | 16% | 26% | 31% |
| 0.045% gellan gum | 11% | 9% | 16% | 28% | 36% |
| 0.1% gellan gum | 0% | 10% | 15% | 21% | 54% |
| 0.2% gellan gum | 2% | 11% | 13% | 23% | 51% |
| 0.4% gellan gum | 0% | 8% | 9% | 13% | 70% |

The results showed that 0.1% gellan gum was able to decrease the incidence of diarrhea to 10% compared to 27% in the control. There were little to no incidence of a stool rating of 1 (watery diarrhea).

\* \* \* \*

All the references cited above are incorporated by reference into this patent.

The words "comprise", "comprises", and "comprising" are to be interpreted inclusively rather than exclusively.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore is not limited to the above embodiments, and may be variously modified.

We claim:

1. A composition for animal consumption, wherein the composition comprises:
    at least one food component;
    at least about 0.1% of a microbial exopolysaccharide (based on the dry weight of the composition); and
    protein, fat, crude fiber, moisture, ash, calcium, magnesium, phosphorous, potassium, sodium, and chloride,
    wherein the microbial exopolysaccharide is coated on the surface of the food and wherein the composition is a pet food composition, and wherein the composition is administered to a dog or a cat in an amount of at least 0.05 g/kg.

2. The composition as set forth in claim 1, wherein the composition comprises from about 0.1% to about 4% of a microbial exopolysaccharide (based on the dry weight of the composition).

3. The composition as set forth in claim 1, wherein the food component is selected from the group consisting of meat, a meat product, a dairy product and an egg product.

4. The composition as set forth in claim 1, wherein the microbial exopolysaccharide comprises a gellan gum.

5. The composition of claim 4, wherein the composition comprises 0.1% to 4% by weight of gellan gum.

6. The composition of claim 5, wherein the composition comprises at least 0.5% by weight gellan gum.

7. A composition for animal consumption, wherein the composition comprises
    at least one food component;
    at least about 0.1% of a microbial exopolysaccharide (based on the dry weight of the composition), and
    the following by weight of the composition
        Protein 7.94%,
        Fat 9.85%,
        Crude Fiber 0.2%,
        Moisture 72.6%,
        Ash 2.11%,
        Calcium 0.5%,
        Magnesium 0.024%,
        Phosphorus 0.26%,
        Potassium 0.24%,
        Sodium 0.094%, and
        Chloride 0.23%;
    wherein the microbial exopolysaccharide is coated on the surface of the food and wherein the composition is a pet food composition.

\* \* \* \* \*